(12) United States Patent
Burton, Jr. et al.

(10) Patent No.: US 7,459,073 B2
(45) Date of Patent: *Dec. 2, 2008

(54) HYDROCARBON CONVERSION USING MOLECULAR SIEVE SSZ-47B

(75) Inventors: Allen W. Burton, Jr., Richmond, CA (US); Stacey I. Zones, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 10/745,746

(22) Filed: Dec. 23, 2003

(65) Prior Publication Data

US 2005/0133413 A1   Jun. 23, 2005

(51) Int. Cl.
*C10G 47/16* (2006.01)
*C10G 73/38* (2006.01)
*C10G 11/05* (2006.01)
*C10G 35/095* (2006.01)
*C07C 2/12* (2006.01)
*C07C 2/66* (2006.01)
*C07C 4/18* (2006.01)

(52) U.S. Cl. .............. 208/111.01; 208/27; 208/46; 208/58; 208/120.01; 208/137; 585/407; 585/446; 585/475; 585/533; 585/640; 585/671; 585/739; 423/706; 423/708; 423/718

(58) Field of Classification Search ............... 208/46, 208/27, 58, 120.01, 137; 423/706, 718, 708; 585/407, 446, 475, 533, 640, 671, 739
See application file for complete search history.

(56) References Cited

U.S. PATENT DOCUMENTS

| 5,785,947 | A | | 7/1998 | Zones et al. | |
| 5,958,370 | A | * | 9/1999 | Zones et al. | ............. 423/706 |
| 6,156,290 | A | | 12/2000 | Lee et al. | |
| 6,540,903 | B2 | * | 4/2003 | Lee et al. | ............. 208/46 |
| 7,063,828 | B2 | * | 6/2006 | Burton et al. | ............. 423/706 |

* cited by examiner

*Primary Examiner*—Glenn Caldarola
*Assistant Examiner*—Prem C. Singh
(74) *Attorney, Agent, or Firm*—Richard J. Sheridan; Susan Abernathy

(57) ABSTRACT

The present invention relates to new crystalline molecular sieve SSZ-47B prepared using a N-cyclopentyl-1,4-diazabicyclo[2.2.2]octane cation as a structure-directing agent and an amine too large to fit in the pores of the molecular sieve nonasil, methods for synthesizing SSZ-47B and processing employing SSZ-47B in a catalyst.

65 Claims, 3 Drawing Sheets

SSZ-47B calcined

HYDROCARBON CONVERSION USING MOLECULAR SIEVE SSZ-47B

BACKGROUND OF THE INVENTION

1. Field of the Invention

The present invention relates to crystalline molecular sieve SSZ-47B having high micropore volume and high catalytic activity, and a method for preparing such high micropore volume, highly active SSZ-47B using N-cyclopentyl-1,4-diazabicyclo[2.2.2] octane cation (referred to herein as "N-cyclopentyl DABCO cation") structure directing agent (SDA) in the presence of an amine too large to fit in the pores of the molecular sieve nonasil, a clathrasil material.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

SUMMARY OF THE INVENTION

The present invention is directed to a family of crystalline molecular sieves with unique properties, referred to herein as "molecular sieve SSZ-47B" or simply "SSZ-47B". Preferably, SSZ-47B is obtained in its silicate, aluminosilicate, titanosilicate, germanosilicate, vanadosilicate or borosilicate form. The term "silicate" refers to a molecular sieve having a high mole ratio of silicon oxide relative to aluminum oxide (or other metal oxide), preferably a mole ratio greater than 100, including molecular sieves comprised entirely of silicon oxide. As used herein, the term "aluminosilicate" refers to a molecular sieve containing both aluminum oxide and silicon oxide and the term "borosilicate" refers to a molecular sieve containing oxides of both boron and silicon.

Molecular sieves, including zeolites, are typically synthesized by using a structure directing agent ("SDA", sometimes called a templating agent) in the reaction mixture used to make the molecular sieve. The SDA is believed to "direct" the formation of the molecular sieve's crystal structure as the pores of the molecular sieve form. As such, the SDA must be small enough to fit within the pores of the desired molecular sieve.

U.S. Pat. No. 6,156,290, issued Dec. 5, 2000 to Lee et al., discloses zeolite SSZ-47 and a method of making it using a 3(trimethylammonium) -bicyclo[3.2.1]octane ammonium cation or N,N-dimethyl-3-azoniabicyclo[4.2.1]nonane cation as an SDA. However, when each of these cations alone is used as the SDA, significant amounts of nonasil can form as an intergrowth in the crystal structure of the SSZ-47.

U.S. Pat. No. 5,785,947, issued Jul. 28, 1998 to Zones et al., discloses the preparation of zeolites using a small quantity of an SDA and a larger quantity of an amine component containing at least one amine having from one to eight carbon atoms, ammonium hydroxide or mixtures thereof. It is believed that the amines disclosed in U.S. Pat. No. 5,785,947 are all small enough to fit in the pores of nonasil and, therefore, would not prevent the intergrowth of nonasil during the preparation of SSZ-47B.

It has now been found that SSZ-47B can be synthesized while preventing the formation of nonasil intergrowth. This is accomplished by including in the reaction mixture, along with the SDA, a neutral amine that is too large to fit in the pores of nonasil. Preferably, the amine is also small enough to fit in the pores of SSZ-47B. In addition to preventing the formation of nonasil intergrowth, it has been discovered that the SSZ-47B made in accordance with this invention has a micropore volume and catalytic activity approximately double that of the SSZ-47 disclosed in Lee et al.

The diffraction patterns of SSZ-47 and SSZ-47B share similar features with those of the NON/EUO/NES family of zeolites. The powder diffraction patterns of SSZ-47 possess a combination of sharp and broad peaks that are often observed in the powder XRD patterns of disordered or intergrown materials. The diffraction patterns of SSZ-47 exhibit a peak at about 9.5° 2θ which is very close to the 111 peak of nonasil (NON), a clathrasil material with no accessible micropore volume. The intensity and position of this peak vary among different preparations of SSZ-47. However, in contrast with nonasil-type materials, these samples of SSZ-47 possess micropore volumes of 0.06-0.08. This measured micropore volume is lower than those typically measured for medium or large pore zeolites. As the relative intensity of the peak near 9.5° 2θ increases, the measured micropore volume (among different preparations) of the SSZ-47 material decreases. These data are consistent with an increase in the fraction of nonasil or other clathrasil-like domains within the zeolite. These data suggest SSZ-47 may contain clathrasil-like domains intergrown with EUO- and/or NES-type domains or with domains of other 10-ring and/or 12-ring pore zeolites.

The samples of SSZ-47 are prepared using a combination of a quaternary ammonium compound and isobutylamine as structure directing agents. When these samples are calcined in the presence of oxygen, the resulting materials are often discolored. This result indicates there may be organic molecules occluded within cage structures that do not allow access to small molecules such as oxygen. The largest dimensions of the nonasil cage parallel to the orthorhombic axes of the crystal structure are 8.9 (y-axis)×8.4 (x-axis)×6.5 Å (z-axis). These dimensions are determined by subtracting the ionic radii of the oxygen atoms (1.35 Å) from the distances between the centers of opposing oxygen atoms. Since the dimensions of the quaternary ammonium compounds are too large to allow their occlusion within nonasil-type cages, it is likely that the smaller isobutylamine molecules are occluded within these small cages. This suggests that amines too large to fit within a nonasil cage may prevent the creation of these cage structures if they are used in place of isobutylamine in the zeolite syntheses. Since the nonasil cages are not accessible to adsorbing molecules, elimination of the nonasil domains might improve the adsorption or catalytic properties of the material.

It has been found that molecular sieves can be synthesized using a combination of quaternary ammonium compounds with a large, neutral amine. Although the diffraction patterns of these materials are similar to those of SSZ-47, they do not possess the 111 peak of nonasil and the measured micropore volumes of these materials are appreciably greater than those of SSZ-47. These improved materials collectively are referred to herein as "SSZ-47B."

In accordance with the present invention, there is provided a molecular sieve having a mole ratio greater than about 15 of (1) an oxide of a first tetravalent element to (2) an oxide of a trivalent element, pentavalent element, second tetravalent element different from said first tetravalent element or mixture thereof having, after calcination, the X-ray diffraction lines of Table II.

The present invention further provides a molecular sieve having a mole ratio greater than about 15 of (1) an oxide of silicon, germanium or mixtures thereof to (2) an oxide of aluminum, gallium, iron, boron, titanium, indium, vanadium or mixtures thereof having, after calcination, the X-ray diffraction lines of Table II. The present invention also provides such a molecule sieve having a micropore volume of at least 0.10. Further provided is such a molecular sieve having a Constraint Index of less than or equal to 2.0.

For high catalytic activity, the SSZ-47B molecular sieve should be predominantly in its hydrogen ion form. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

In accordance with the present invention there is provided a process for converting hydrocarbons comprising contacting a hydrocarbonaceous feed at hydrocarbon converting conditions with a catalyst comprising the molecular sieve of this invention. The molecular sieve may be predominantly in the hydrogen form. It may also be substantially free of acidity.

Further provided by the present invention is a hydrocracking process comprising contacting a hydrocarbon feedstock under hydrocracking conditions with a catalyst comprising the molecular sieve of this invention, preferably predominantly in the hydrogen form.

This invention also includes a dewaxing process comprising contacting a hydrocarbon feedstock under dewaxing conditions with a catalyst comprising the molecular sieve of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the molecular sieve of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising the molecular sieve of this invention. The molecular sieve may be predominantly in the hydrogen form. The catalyst may contain at least one Group VIII metal.

In accordance with this invention, there is also provided a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) with a catalyst comprising the molecular sieve of this invention, preferably predominantly in the hydrogen form. The catalyst may contain at least one Group VIII metal. The catalyst may be a layered catalyst comprising a first layer comprising the molecular sieve of this invention, and a second layer comprising an aluminosilicate molecular sieve which is more shape selective than the molecular sieve of said first layer. The first layer may contain at least one Group VIII metal.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. (204° C.) and at a pressure of from about 15 psig to about 3000 psig (0.103-20.7 Mpa gauge) in the presence of added hydrogen gas with a catalyst comprising the molecular sieve of this invention. The molecular sieve may be predominantly in the hydrogen form. The catalyst may contain at least one Group VIII metal.

Further included in this invention is a process for isomerization dewaxing a raffinate comprising contacting said raffinate in the presence of added hydrogen with a catalyst comprising the molecular sieve of this invention. The raffinate may be bright stock, and the molecular sieve may be predominantly in the hydrogen form. The catalyst may contain at least one Group VIII metal.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the molecular sieve of this invention made substantially free of acidity by neutralizing said molecular sieve with a basic metal. Also provided in this invention is such a process wherein the molecular sieve contains a Group VIII metal component.

Also provided by the present invention is a catalytic cracking process comprising contacting a hydrocarbon feedstock in a reaction zone under catalytic cracking conditions in the absence of added hydrogen with a catalyst comprising the molecular sieve of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the molecular sieve of this invention, preferably predominantly in the hydrogen form. The molecular sieve may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the molecular sieve of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, naphthalene, naphthalene derivatives, dimethylnaphthalene or mixtures thereof.

The present invention also provides a process for alkylating an aromatic hydrocarbon which comprises contacting under alkylation conditions an aromatic hydrocarbon with a $C_{20+}$ olefin under at least partial liquid phase conditions and in the presence of a catalyst comprising the molecular sieve of this invention, preferably predominantly in the hydrogen form. The aromatic hydrocarbon and olefin are present in a molar ratio of about 1:15 to about 25:1, respectively. The aromatic hydrocarbon is selected from the group consisting of benzene, toluene, ethylbenzene, xylene, naphthalene, naphthalene derivatives, dimethylnaphthalene or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the molecular sieve of this invention, preferably predominantly in the hydrogen form. The aromatic hydrocarbon and the polyalkyl aromatic hydrocarbon may be present in a molar ratio of from about 1:1 to about 25:1, respectively.

The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the molecular sieve of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the molecular sieve of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the molecular sieve of this invention.

The present invention further provides a process for oligomerizing olefins comprising contacting an olefin feed under oligomerization conditions with a catalyst comprising the molecular sieve of this invention.

This invention also provides a process for converting oxygenated hydrocarbons comprising contacting said oxygenated hydrocarbon with a catalyst comprising the molecular sieve of this invention under conditions to produce liquid products. The oxygenated hydrocarbon may be a lower alcohol.

Further provided in accordance with the present invention is a process for the production of higher molecular weight hydrocarbons from lower molecular weight hydrocarbons comprising the steps of:
(a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
(b) withdrawing from said reaction zone a higher molecular weight hydrocarbon-containing stream.

DETAILED DESCRIPTION OF THE INVENTION

Figure 1:
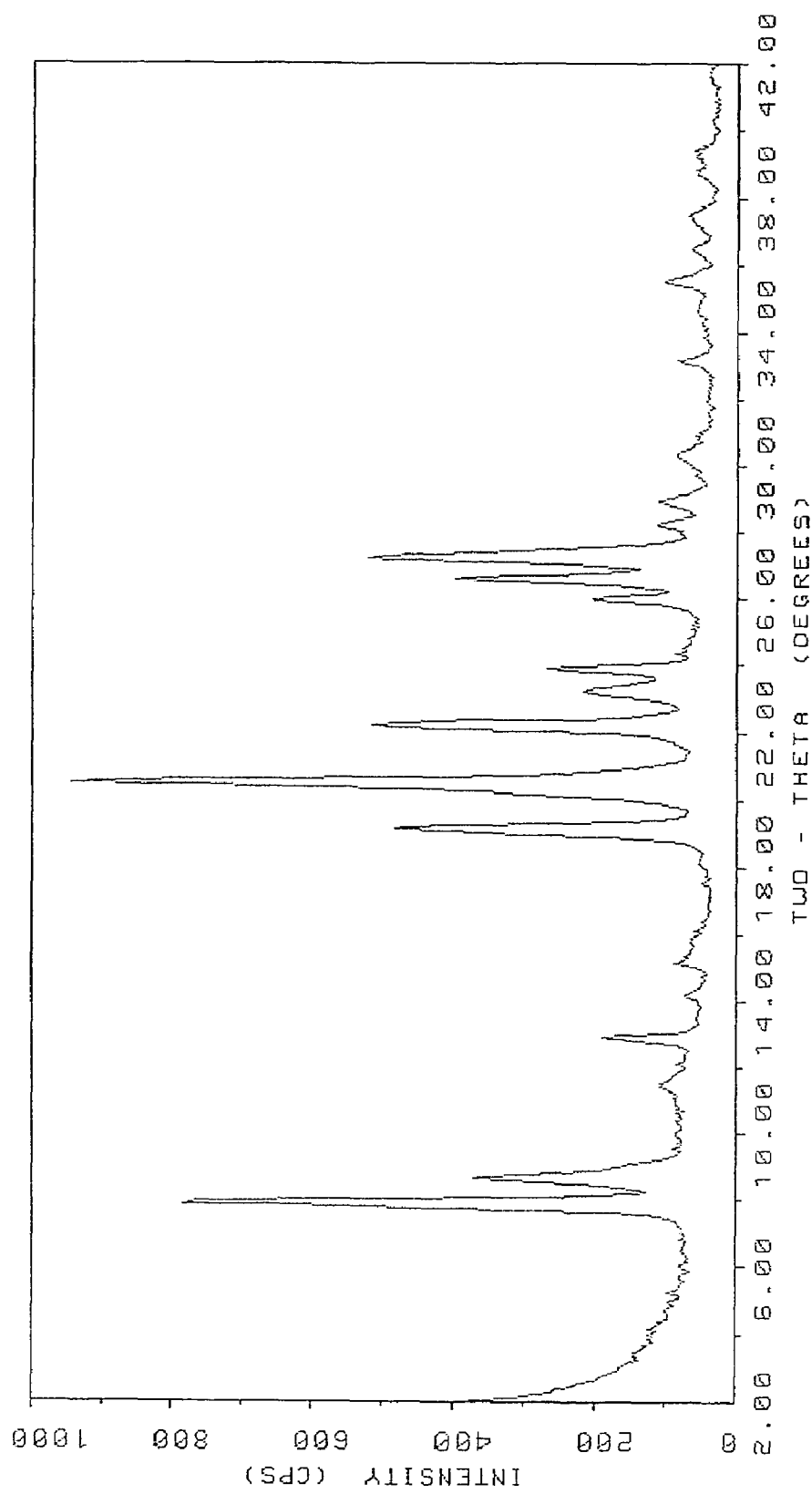
FIG. 1 is an X-ray diffraction pattern of SSZ-47B after it has been calcined.

The present invention comprises a family of crystalline, large pore molecular sieves designated herein "molecular sieve SSZ-47B" or simply "SSZ-47B". As used herein, the term "large pore" means having an average pore size diameter greater than about 6.0 Angstroms, preferably from about 6.5 Angstroms to about 7.5 Angstroms.

In preparing SSZ-47B, a N-cyclopentyl DABCO cation is used as a structure directing agent ("SDA"), also known as a crystallization template. The N-cyclopentyl DABCO cation has the following structure:

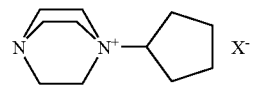

N-cyclopentyl DABCO cation can be prepared as described in U.S. Pat. No. 6,033,643, issued Mar. 7, 2000 to Yuen et al., which is incorporated by reference in its entirety.

The SDA cation is associated with an anion ($X^-$) which may be any anion that is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

The amine used in combination with the N-cyclopentyl DABCO SDA is large enough that it will not fit in the pores of the molecular sieve nonasil. Preferably, it is also small enough that it does fit in the pores of SSZ-47B. An example of such an amine is 4,4'-trimethylene dipiperidine which has the structure

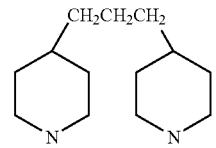

4,4'-trimethylene dipiperidine

In general, SSZ-47B is prepared by contacting an active source of one or more oxides selected from the group consisting of monovalent element oxides, divalent element oxides, trivalent element oxides, tetravalent element oxides and/or pentavalent elements with the SDA and amine.

SSZ-47B is prepared from a reaction mixture having the composition shown in Table A below.

TABLE A

| | Reaction Mixture | |
|---|---|---|
| | Typical | Preferred |
| $YO_2/W_aO_b$ | >15 | 30-70 |
| $OH^-/YO_2$ | 0.10-0.50 | 0.20-0.30 |
| $Q/YO_2$ | 0.05-0.50 | 0.10-0.20 |
| $M_{2/n}/YO_2$ | 0.02-0.40 | 0.10-0.25 |
| $H_2O/YO_2$ | 30-80 | 35-45 |
| Amine/$YO_2$ | 0.05-0.50 | 0.10-0.20 | where Y, W, Q, M, n and Amine are as defined above, and a is 1 or 2, and b is 2 when a is 1 (i.e., W is tetravalent) and b is 3 when a is 2 (i.e., W is trivalent).

In practice, SSZ-47B is prepared by a process comprising:
(a) preparing an aqueous solution containing sources of at least one oxide capable of forming a crystalline molecular sieve, a N-cyclopentyl DABCO cation having an anionic counterion which is not detrimental to the formation of SSZ-47B, and an amine too large to fit in the pores of the molecular sieve nonasil;

(b) maintaining the aqueous solution under conditions sufficient to form crystals of SSZ-47B; and (c) recovering the crystals of SSZ-47B.

Accordingly, SSZ-47B may comprise the crystalline material, the SDA and the amine in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a trivalent element(s), pentavalent element(s), second tetravalent element(s) different from the first tetravalent element(s) or mixture thereof. The first tetravalent element(s) is preferably selected from the group consisting of silicon, germanium and combinations thereof. More preferably, the first tetravalent element is silicon. The trivalent element, pentavalent element and second tetravalent element (which is different from the first tetravalent element) is preferably selected from the group consisting of aluminum, gallium, iron, boron, titanium, indium, vanadium and combinations thereof. More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides. Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The SDA may be used to provide hydroxide ion. Thus, it may be beneficial to ion exchange, for example, the halide to hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-47B are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the molecular sieve is prepared using mild stirring or agitation.

During the hydrothermal crystallization step, the SSZ-47B crystals can be allowed to nucleate spontaneously from the reaction mixture. The use of SSZ-47B crystals as seed material can be advantageous in decreasing the time necessary for complete crystallization to occur. In addition, seeding can lead to an increased purity of the product obtained by promoting the nucleation and/or formation of SSZ-47B over any undesired phases. When used as seeds, SSZ-47B crystals are added in an amount between 0.1 and 10% of the weight of first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-47B crystals. The drying step can be performed at atmospheric pressure or under vacuum.

SSZ-47B as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 15, and has, after calcination, the X-ray diffraction lines of Table II below. SSZ-47B further has a composition, as synthesized (i.e., prior to removal of the SDA from the SSZ-47B) and in the anhydrous state, in terms of mole ratios, shown in Table B below.

TABLE B

| As-Synthesized SSZ-47B | |
|---|---|
| $YO_2/W_cO_d$ | >15 |
| $M_{2/n}/YO_2$ | 0.01-0.03 |
| $Q/YO_2$ | 0.02-0.05 |
| $Amine/YO_2$ | 0.01-0.05 | where Y, W, c, d, M, n, Q and Amine are as defined above.

$^{13}C$ MASNMR analysis of as-synthesized SSZ-47B provides evidence that the as-synthesized SSZ-47B contains both the N-cyclopentyl DABCO SDA and the amine inside the molecular sieve. This is also evidence that the amine is small enough to fit in the pores of SSZ-47B.

SSZ-47B can be made with a mole ratio of $YO_2/W_cO_d$ of ∞, i.e., there is essentially no $W_cO_d$ present in the SSZ-47B. In this case, the SSZ-47B would be an all-silica material or a germanosilicate. Thus, in a typical case where oxides of silicon and aluminum are used, SSZ-47B can be made essentially aluminum free, i.e., having a silica to alumina mole ratio of ∞. A method of increasing the mole ratio of silica to alumina is by using standard acid leaching or chelating treatments. Essentially aluminum-free SSZ-47B can be synthesized using essentially aluminum-free silicon sources as the main tetrahedral metal oxide component in the presence of boron. The boron can then be removed, if desired, by treating the borosilicate SSZ-47B with acetic acid at elevated temperature (as described in Jones et al., *Chem. Mater.*, 2001, 13, 1041-1050) to produce an all-silica version of SSZ-47B. SSZ-47B can also be prepared directly as a borosilicate. If desired, the boron can be removed as described above and replaced with metal atoms by techniques known in the art to make, e.g., an aluminosilicate version of SSZ-47B. SSZ-47B can also be prepared directly as an aluminosilicate.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

SSZ-47B, as-synthesized, has a crystalline structure whose X-ray powder diffraction pattern exhibit the characteristic lines shown in Table I and is thereby distinguished from other molecular sieves.

TABLE I

As-Synthesized SSZ-47B

| 2 Theta[a] | d-spacing (Angstroms) | Relative Intensity (%)[b] |
|---|---|---|
| 7.80 | 11.3 | S |
| 8.54 | 10.4 | W-M |
| 19.02 | 4.67 | M |
| 20.36 | 4.36 | VS |
| 22.10 | 4.02 | S-VS |
| 23.06 | 3.86 | M |
| 23.74 | 3.75 | M |
| 25.92 | 3.44 | W-M |
| 26.46 | 3.37 | W |
| 27.10 | 3.29 | S |

[a] ±0.1
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Figure 2:
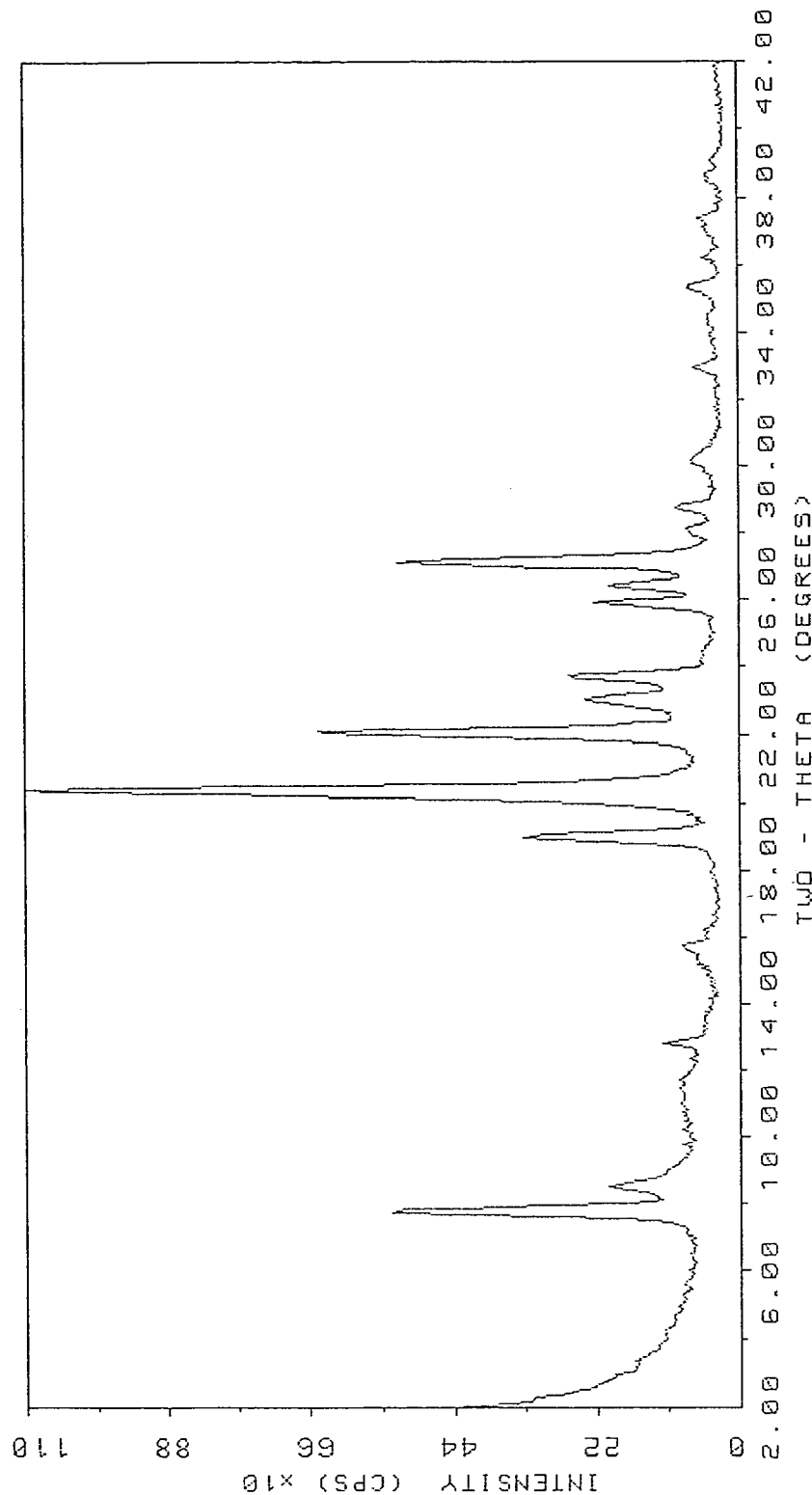
FIG. 2 is an X-ray diffraction pattern of SSZ-47B in the as-made form, i.e., prior to removal of the SDA from SSZ-47B.

Table IA below shows the X-ray powder diffraction lines for as-synthesized SSZ-47B including actual relative intensities (See FIG. 2).

TABLE IA

| 2 Theta[a] | d-spacing (Angstroms) | Relative Intensity (%) |
|---|---|---|
| 7.80 | 11.3 | 49 |
| 8.54 | 10.4 | 19 |
| 12.82 | 6.91 | 11 |
| 15.74 | 5.63 | 8 |
| 19.02 | 4.67 | 30 |
| 20.36 | 4.36 | 100 |
| 22.10 | 4.02 | 59 |
| 23.06 | 3.86 | 22 |
| 23.74 | 3.75 | 24 |
| 25.92 | 3.44 | 20 |
| 26.46 | 3.37 | 18 |
| 27.10 | 3.29 | 48 |
| 28.10 | 3.18 | 7 |
| 28.76 | 3.10 | 9 |
| 30.22 | 2.96 | 6 |
| 32.98 | 2.72 | 6 |
| 35.42 | 2.53 | 7 |
| 36.22 | 2.48 | 5 |
| 36.99 | 2.43 | 2 |
| 37.34 | 2.41 | 5 |
| 38.72 | 2.33 | 5 |
| 39.08 | 2.30 | 4 |

[a] ±0.1

Figure 3:
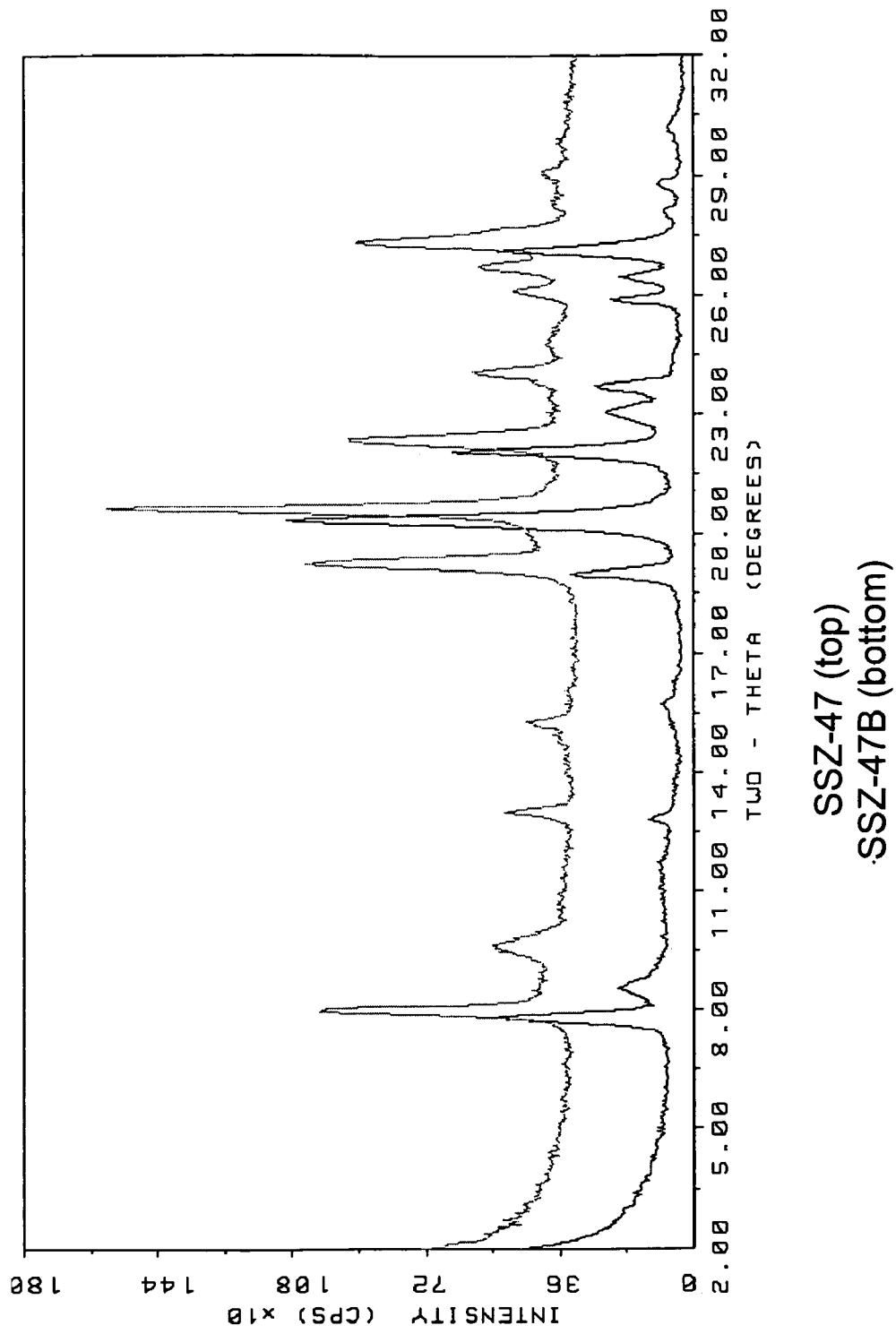
FIG. 3 shows two X-ray diffraction patterns, the top one being SSZ-47 and the bottom one being SSZ-47B.

After calcination, the SSZ-47B molecular sieves have a crystalline structure whose X-ray powder diffraction pattern include the characteristic lines shown in Table II (See FIG. 1). FIG. 3 shows a comparison of relative intensities of SSZ-47 (top) and SSZ-47B (bottom):

TABLE II

Calcined SSZ-47B

| 2 Theta[a] | d-spacing (Angstroms) | Relative Intensity (%) |
|---|---|---|
| 7.91 | 11.18 | S |
| 8.68 | 10.19 | M |
| 19.14 | 4.64 | M-S |
| 20.51 | 4.33 | VS |
| 22.23 | 4.00 | S |
| 23.27 | 3.82 | M |
| 23.9 | 3.72 | W |
| 26 | 3.43 | W |
| 26.62 | 3.35 | M |
| 27.26 | 3.27 | S |

[a] ±0.1

Table IIA below shows the X-ray powder diffraction lines for calcined SSZ-47B including actual relative intensities.

TABLE IIA

| 2 Theta[a] | d-spacing (Angstroms) | Relative Intensity (%) |
|---|---|---|
| 7.91 | 11.18 | 57.4 |
| 8.68 | 10.19 | 34.1 |
| 9.025 | 9.80 | 6.9 |
| 11.42 | 7.75 | 5.6 |
| 12.91 | 6.86 | 9.9 |
| 14.2 | 6..24 | 3.4 |
| 15.22 | 5.82 | 4.2 |
| 15.77 | 5.62 | 5.2 |
| 19.14 | 4.64 | 40.6 |
| 20.51 | 4.33 | 100.0 |
| 22.23 | 4.00 | 47.2 |
| 23.27 | 3.82 | 22.2 |
| 23.9 | 3.72 | 18.4 |
| 26 | 3.43 | 10.8 |
| 26.62 | 3.35 | 25.9 |
| 27.26 | 3.27 | 60.8 |
| 28.26 | 3.16 | 4.7 |
| 28.97 | 3.08 | 6.2 |
| 30.33 | 2.95 | 8.8 |
| 30.95 | 2.89 | 0.8 |
| 33.18 | 2.70 | 4.2 |
| 34.63 | 2.59 | 6.4 |
| 35.56 | 2.52 | 8.3 |
| 36.51 | 2.46 | 3.4 |
| 37.42 | 2.40 | 8.8 |

[a] ±0.1

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

The X-ray diffraction pattern of Table I is representative of "as-synthesized" or "as-made" SSZ-47B molecular sieves. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-47B are shown in Table II. Calcination can also result in changes in the intensities of the peaks as compared to patterns of the "as-made" material, as well as minor shifts in the diffraction pattern. The molecular sieve produced by exchanging the metal or other cations present in the molecular sieve with various other cations (such as H$^+$ or NH$_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-47B can be used as-synthesized, but preferably will be thermally treated (calcined). Usually, it is desirable to remove the alkali metal cation by ion exchange and replace it with hydrogen, ammonium, or any desired metal ion. The molecular sieve can be leached with chelating agents, e.g., EDTA or dilute acid solutions, to increase the silica to alumina mole ratio. The molecular sieve can also be steamed; steaming helps stabilize the crystalline lattice to attack from acids.

The molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-47B. The SSZ-47B can also be impregnated with the metals, or the metals can be physically and intimately admixed with the SSZ-47B using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-47B, the spatial arrangement of the atoms which form the basic crystal lattice of the molecular sieve remains essentially unchanged.

SSZ-47B can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-47B can be extruded before drying, or, dried or partially dried and then extruded.

SSZ-47B can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-47B molecular sieves are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-47B are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives, and forming higher molecular weight hydrocarbons from lower molecular weight hydrocarbons (e.g., methane upgrading).

The SSZ-47B catalysts may have high selectivity, and under hydrocarbon conversion conditions can provide a high percentage of desired products relative to total products.

For high catalytic activity, the SSZ-47B molecular sieve should be predominantly in its hydrogen ion form. Generally, the molecular sieve is converted to its hydrogen form by ammonium exchange followed by calcination. If the molecular sieve is synthesized with a high enough ratio of SDA cation to sodium ion, calcination alone may be sufficient. It is preferred that, after calcination, at least 80% of the cation sites are occupied by hydrogen ions and/or rare earth ions. As used herein, "predominantly in the hydrogen form" means that, after calcination, at least 80% of the cation sites are occupied by hydrogen ions and/or rare earth ions.

SSZ-47B molecular sieves can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-47B in the hydrocarbon conversion reactions of this invention. Preferred conditions are indicated in parentheses.

| Process | Temp., °C. | Pressure | LHSV |
|---|---|---|---|
| Hydrocracking | 175-485 | 0.5-350 bar | 0.1-30 |
| Dewaxing | 200-475 (250-450) | 15-3000 psig, 0.103-20.7 Mpa gauge (200-3000, 1.38-20.7 Mpa gauge) | 0.1-20 (0.2-10) |
| Aromatics formation | 400-600 (480-550) | atm.-10 bar | 0.1-15 |
| Cat. Cracking | 127-885 | subatm.-[1] (atm.-5 atm.) | 0.5-50 |
| Oligomerization | 232-649[2] 10-232[4] (27-204)[4] | 0.1-50 atm.[2,3] — — | 0.2-50[2] 0.05-20[5] (0.1-10)[5] |
| Paraffins to aromatics | 100-700 | 0-1000 psig | 0.5-40[5] |
| Condensation of alcohols | 260-538 | 0.5-1000 psig, 0.00345-6.89 Mpa gauge | 0.5-50[5] |
| Isomerization | 93-538 (204-315) | 50-1000 psig, 0.345-6.89 Mpa gauge | 1-10 (1-4) |
| Xylene isomerization | 260-593[2] (315-566)[2] 38-371[4] | 0.5-50 atm.[2] (1-5 atm)[2] 1-200 atm.[4] | 0.1-100[5] (0.5-50)[5] 0.5-50 |

[1] Several hundred atmospheres
[2] Gas phase reaction
[3] Hydrocarbon partial pressure
[4] Liquid phase reaction
[5] WHSV
Other reaction conditions and parameters are provided below.

Hydrocracking

Using a catalyst which comprises SSZ-47B, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No. 4,910,006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-47B, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-47B under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel) (0.089 to 5.34 SCM/liter (standard cubic meters/liter)), preferably about 1000 to about 20,000 SCF/bbl (0.178 to 3.56 SCM/liter). Generally, hydrogen will be separated from the product and recycled to the reaction zone. Typical feedstocks include light gas oil, heavy gas oils and reduced crudes boiling above about 350° F. (177° C.).

A typical dewaxing process is the catalytic dewaxing of a hydrocarbon oil feedstock boiling above about 350° F. (177° C.) and containing straight chain and slightly branched chain hydrocarbons by contacting the hydrocarbon oil feedstock in the presence of added hydrogen gas at a hydrogen pressure of about 15-3000 psi (0.103-20.7 Mpa) with a catalyst comprising SSZ-47B and at least one Group VIII metal.

The SSZ-47B hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isomerization dewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-47B may also be utilized as a dewaxing catalyst in the form of a layered catalyst. That is, the catalyst comprises a first layer comprising molecular sieve SSZ-47B and at least one Group VIII metal, and a second layer comprising an aluminosilicate molecular sieve which is more shape selective than molecular sieve SSZ-47B. The use of layered catalysts is disclosed in U.S. Pat. No. 5,149,421, issued Sep. 22, 1992 to Miller, which is incorporated by reference herein in its entirety. The layering may also include a bed of SSZ-47B layered with a non-zeolitic component designed for either hydrocracking or hydrofinishing.

SSZ-47B may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig (2.76 to 20.7 Mpa gauge) at space velocities (LHSV) between about 0.1 and 20 and a hydrogen recycle rate of about 400 to 1500 SCF/bbl (0.071 to 0.27 SCM/liter). The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-47B. For example, a $C_{20+}$ lube oil may be made by isomerizing a $C_{20+}$ olefin feed over a catalyst comprising SSZ-47B in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. (204° C.) and at a pressure of from about 15 psig to about 3000 psig (0.103-20.7 Mpa gauge) in the presence of added hydrogen gas with a catalyst comprising SSZ-47B in the hydrogen form and at least one Group VIII metal.

Aromatics Formation

SSZ-47B can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-47B. It is also possible to convert heavier feeds into BTX or naphthalene derivatives of value using a catalyst comprising SSZ-47B.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the molecular sieve with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The molecular sieve itself can be substantially free of acidity only at very high silica:alumina mole ratios.

Catalytic Cracking

Hydrocarbon cracking stocks can be catalytically cracked in the absence of hydrogen using SSZ-47B, preferably predominantly in the hydrogen form.

When SSZ-47B is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No 5,316,753. When a traditional cracking catalyst (TC) component is employed, the relative weight ratio of the TC to the SSZ-47B is generally between about 1:10 and about 500:1, desirably between about 1:10 and about 200:1, preferably between about 1:2 and about 50:1, and most preferably is between about 1:1 and about 20:1. The novel molecular sieve and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-47B in the hydrogen form, with a hydrocarbon feed under isomerization conditions. The feed is preferably a light straight run fraction, boiling within the range of 30° F. to 250° F. (−1° C. to 121° C.) and preferably from 60° F. to 200° F. (16° C. to 93° C.). Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-47B can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-47B.

SSZ-47B can also be used for removing benzene from gasoline by alkylating the benzene as described above and removing the alkylated product from the gasoline.

For high catalytic activity, the SSZ-47B molecular sieve should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene or naphthalene derivatives such as dimethylnaphthalene may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about 4 carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F. (38° C. to 315° C.), preferably 250° F. to 450° F. (121° C. to 232° C.). The reaction pressure should be sufficient to maintain at least a partial liquid phase in order to retard catalyst fouling. This is typically 50 psig to 1000 psig (0.345 to 6.89 Mpa gauge) depending on the feedstock and reaction temperature. Contact time may range from 10 seconds to 10 hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F. (38° C. to 315° C.), but it is preferably about 250° F. to 450° F. (121° C. to 232° C.). The reaction pressure should be sufficient to maintain at least a partial liquid phase, typically in the range of about 50 psig to 1000 psig (0.345 to 6.89 Mpa gauge), preferably 300 psig to 600 psig (2.07 to 4.14 Mpa gauge). The weight hourly space velocity will range from about 0.1 to 10. U.S. Pat. No. 5,082,990 issued on Jan. 21, 1992 to Hsieh, et al. describes such processes and is incorporated herein by reference.

SSZ-47B can also be used to alkylate aromatics compounds using $C_{20+}$ olefins. These alkylated aromatics can then be converted to sulfonic acids or sulfonates and used as additives in lubricating oils. Such an alkylation process is disclosed in U.S. Pat. No. 5,922,922, issued Jul. 13, 1999 to Harris et al., which is incorporated by reference in its entirety.

The aromatic hydrocarbon that is alkylated in this process is preferably benzene or toluene, but a higher molecular weight hydrocarbon may also be used. The feed aromatic hydrocarbon may, therefore be benzene, toluene, xylene, naphthalene, etc. Preferably it is benzene or toluene, because the resulting alkylates are more easily processed into the corresponding sulfonic acids or LOB or HOB sulfonates.

The olefinic hydrocarbons that are consumed in the process are normal alpha-olefins (NAO) that may have from about six to thirty carbon atoms per molecule. Preferably, they have about fourteen to thirty carbon atoms per molecule. Most preferably, they are predominantly alpha olefins having from twenty to twenty-eight carbon atoms per molecule.

The NAO is isomerized with an acidic catalyst prior to alkylation. Preferably, the catalyst is a molecular sieve with a one-dimensional pore system such as SM-3, MAPO-11, SAPO-11, SSZ-32, ZSM-23, MAPO-39, SAPO-39, ZSM-22 and SSZ-20. Other possible solid acidic catalysts include ZSM-35, SUZ-4, NU-23, NU-87 and natural or synthetic ferrierites.

The isomerization process conditions are well known in the art. See, for example, aforementioned U.S. Pat. No. 5,922, 922.

SSZ-47B, in acidic form, is used as the alkylation catalyst. Preferably, it is used predominantly in the hydrogen form.

The alkylation process conditions are likewise well known in the art. The alkylation reaction is typical carried out with an aromatic to olefin mole ratio from 1:15 to 25:1. Process temperatures can range from 100° C. to 250° C. As the olefins have a high boiling point, the process is preferably carried out in the liquid phase.

Conversion of Paraffins to Aromatics

SSZ-47B can be used to convert light gas $C_2$-$C_6$ paraffins to higher molecular weight hydrocarbons including aromatic compounds. Preferably, the molecular sieve will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Isomerization of Olefins

SSZ-47B can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40-60 weight percent normal butenes. A methyl-tert-butyl ether unit effluent typically contains 40-100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-47B. The process may be carried out generally at a temperature from about 625° F. to about 950° F. (329-510° C.), for butenes, preferably from about 700° F. to about 900° F. (371-482° C.), and about 350° F. to about 650° F. (177-343° C.) for pentenes and hexenes. The pressure ranges from subatmospheric to about 200 psig (1.38 Mpa gauge), preferably from about 15 psig to about 200 psig (0.103 to 1.38 Mpa gauge), and more preferably from about 1 psig to about 150 psig (0.00689 to 1.03 Mpa gauge).

The liquid hourly space velocity during contacting is generally from about 0.1 to about 50 $hr^{-1}$, based on the hydrocarbon feed, preferably from about 0.1 to about 20 $h^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Xylene Isomerization

SSZ-47B may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt. % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt. of a diluent such as toluene, trimethylbenzene, naphthenes or paraffins.

Oligomerization

It is expected that SSZ-47B can also be used to oligomerize straight and branched chain olefins having from about 2 to 21 and preferably 2-5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-47B.

The molecular sieve can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the molecular sieve have a fairly low aromatization activity, i.e., in which the amount of aromatics produced is not more than about 20% by weight. This is accomplished by using a molecular sieve with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such molecular sieves may be obtained by steaming, by use in a conversion process or by any other method which may occur to one skilled in this art.

Condensation of Alcohols

SSZ-47B can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Methane Upgrading

Higher molecular weight hydrocarbons can be formed from lower molecular weight hydrocarbons by contacting the lower molecular weight hydrocarbon with a catalyst comprising SSZ-47B and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide, actinide, molybdenum and/or niobium metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

EXAMPLES

The following examples demonstrate but do not limit the present invention.

Example 1

A reaction mixture is prepared in the Teflon cup of a Parr 23 ml reactor by combining the following: 2 millimoles (0.42 gram) of 4,4'-trimethylene dipiperidine, 1.0 millimole of N-cyclopentyl DABCO hydroxide in a total of 9.25 grams of water, 0.088 gram of Reheis F-2000 alumina (53-56 wt. % $Al_2O_3$), 3 grams of 1 N KOH and 0.90 gram of Cabosil M-5 fumed silica. The first two components represent the amine that is too large to form nonasil and the SDA that forms SSZ-47B, respectively. The reaction mixture is heated at 170° C. while being tumbled at 43 RPM. The reaction mixture has a silica/alumina mole ratio (SAR) of 32. The SSZ-47B product (identified by X-ray diffraction) forms after nine days.

Example 2

The reaction of Example 1 is repeated, except the alumina content is reduced to 0.066 gram. The SAR of the reaction mixture is 40. The reaction produces SSZ-47B (identified by X-ray diffraction).

Example 3

The reaction of Example 1 is repeated, except the alumina content is reduced to 0.044 gram. The SAR of the reaction mixture is 64. The reaction produces SSZ-47B with a little quartz impurity (identified by X-ray diffraction).

Example 4

The reaction of Example 1 is repeated, except the N-cyclopentyl DABCO hydroxide content is reduced to 0.5 millimole. The reaction produces SSZ-47B (identified by X-ray diffraction).

Example 5

The reaction of Example 4 is repeated, except that the reaction mixture is seeded with 2 wt. % (based on the weight of silica) SSZ-47B crystals from the product of Example 1. The reaction produces SSZ-47B (identified by X-ray diffraction).

Example 6

Calcination of SSZ-47B

SSZ-47B as synthesized in Example 3 is calcined to remove the structure directing agent (SDA) and amine. A thin bed of SSZ-47B in a calcination dish is heated in a muffle furnace from room temperature to 120° C. at a rate of 1° C./minute and held for 2 hours. Then, the temperature is ramped up to 540° C. at a rate of 1° C./minute and held for 5 hours. The temperature is ramped up again at 1° C./minute to 595° C. and held there for 5 hours. A 50/50 mixture of air and nitrogen passes through the muffle furnace at a rate of 20 standard cubic feet (0.57 standard cubic meters) per minute during the calcination process.

Example 7

Ammonium-Ion Exchange of SSZ-47B

The $Na^+$ form of SSZ-47B (prepared as in Example 3 or as in Example 5 and calcined as in Example 6) is converted to $NH_4^+$-SSZ-47B form by heating the material in an aqueous solution of $NH_4NO_3$ (typically 1 gm $NH_4NO_3$/1 gm SSZ-47B in 20 ml $H_2O$) at 90° C. for 2-3 hours. The mixture is then filtered and the obtained $NH_4$-exchanged-product is washed with de-ionized water and dried. The ion exchange procedure is repeated again. The $NH_4^+$ form of SSZ-47B can be converted to the $H^+$ form by calcination (as described in Example 6) to 540° C.

Example 8

Nitrogen Adsorption Analysis

The hydrogen form of the products of Example 3 (after a treatment as in Examples 6 and 7 is subjected to a micropore volume analysis using nitrogen as adsorbate and via the BET method. The micropore volume is 0.153 cc/g, thus exhibiting considerable void volume.

Example 9

Constraint Index

The hydrogen form of SSZ-47B of Example 3 (after treatment according to Examples 6 and 7) is pelletized at 3 KPSI, crushed and granulated to 20-40 mesh. A 0.6 gram sample of the granulated material is calcined in air at 540° C. for 4 hours and cooled in a desiccator to ensure dryness. Then, 0.5 gram is packed into a ⅜ inch stainless steel tube with alundum on both sides of the molecular sieve bed. A Lindburg furnace is used to heat the reactor tube. Helium is introduced into the reactor tube at 10 cc/min. and at atmospheric pressure. The reactor is heated to about 315° C., and a 50/50 feed of n-hexane and 3-methylpentane is introduced into the reactor at a rate of 8 μl/min. The feed is delivered by a Brownlee pump. Direct sampling into a GC begins after 10 minutes of feed introduction. The Constraint Index (CI) value is calculated from the GC data using methods known in the art. SSZ-47B has a CI of 1.5 and a conversion at 600° F. (315° C.) of 80.6% after 20 minutes on stream. The data suggests a large pore molecular sieve.

Example 10

Hydrocracking of n-Hexadecane

A 1 gm sample of SSZ-47B (prepared as in Example 3 and treated as in Examples 6 and 7) is suspended in 10 gm de-ionized water. To this suspension, a solution of Pd(NH$_3$)$_4$(NO$_3$)$_2$ at a concentration which would provide 0.5 wt. % Pd with respect to the dry weight of the molecular sieve sample is added. The pH of the solution is adjusted to pH of ~9 by a drop-wise addition of dilute ammonium hydroxide solution. The mixture is then stirred at room temperature for 48 hours. The mixture is then filtered through a glass frit, washed with de-ionized water, and air-dried. The collected Pd-SSZ-47B sample is slowly calcined up to 482° C. in air and held there for three hours.

The calcined Pd/SSZ-47B catalyst is pelletized in a Carver Press and granulated to yield particles with a 20/40 mesh size. Sized catalyst (0.5 g) is packed into a ¼ inch OD tubing reactor in a micro unit for n-hexadecane hydroconversion. The table below gives the run conditions and the products data for the hydrocracking test on n-hexadecane.

| | |
|---|---|
| Temperature | 518° F. |
| Time-on-Stream (hrs.) | 98.6-100.1 |
| WHSV | 1.55 |
| PSIG | 1200 |
| Titrated? | No |
| n-16, % Conversion | 95.5 |
| Hydrocracking Conv. | 75.6 |
| Isomerization Selectivity, % | 20.8 |
| Cracking Selectivity, % | 79.2 |
| C$_{4-}$, % | 17.6 |
| C$_{5+}$ | 60.5 |
| C$_5$/C$_4$ | 3.5 |
| C$_{5+}$C$_6$/C$_5$, % | 36.64 |
| DMB/MP | 0.09 |
| Iso/Normal Ratios | |
| C$_4$ i/n | 4.74 |
| C$_5$ i/n | 3.43 |
| C$_6$ i/n | 2.71 |
| C$_7$ i/n | 4.33 |
| C$_8$ i/n | 6.75 |
| C$_9$ i/n | 5.84 |
| C$_{10}$ i/n | 6.17 |
| C$_{11}$ i/n | 6.22 |
| C$_{12}$ i/n | 6.9 |
| C$_{13}$ i/n | 8.37 |
| C$_4$-C$_{13}$ i/n | 4.5 |
| Yield, % | |
| C$_1$ | 0.07 |
| C$_2$ | 0.11 |
| C$_3$ | 1.88 |
| C$_4$ | 15.69 |
| C$_5$ | 13.09 |
| C$_6$ | 9.34 |
| C$_7$-C$_{13}$ | 38.77 |

What is claimed is:

1. A process for converting hydrocarbons comprising contacting a hydrocarbonaceous feed at hydrocarbon converting conditions with a catalyst comprising a molecular sieve having a mole ratio greater than about 15 of (1) an oxide of a first tetravalent element to (2) an oxide of a trivalent element, pentavalent element, second tetravalent element different from said first tetravalent element or mixture thereof having, after calcination, the X-ray diffraction lines of Table II.

2. The process of claim 1 wherein the molecular sieve has a mole ratio greater than about 15 of (1) an oxide of silicon, germanium or mixtures thereof to (2) an oxide of aluminum, gallium, iron, boron, titanium, indium, vanadium or mixtures thereof.

3. The process of claim 2 wherein the molecular sieve comprises an oxide of silicon and an oxide of aluminum.

4. The process of claim 2 wherein the molecule sieve has a micropore volume of at least 0.10.

5. The process of claim 2 wherein the molecular sieve has a Constraint Index of less than or equal to 2.0.

6. The process of claim 1 wherein the molecular sieve is predominantly in the hydrogen form.

7. The process of claim 1 wherein the molecular sieve is substantially free of acidity.

8. The process of claim 1 wherein the process is a hydrocracking process comprising contacting the catalyst with a hydrocarbon feedstock under hydrocracking conditions.

9. The process of claim 8 wherein the molecular sieve is predominantly in the hydrogen form.

10. The process of claim 1 wherein the process is a dewaxing process comprising contacting the catalyst with a hydrocarbon feedstock under dewaxing conditions.

11. The process of claim 10 wherein the molecular sieve is predominantly in the hydrogen form.

12. The process of claim 1 wherein the process is a process for improving the viscosity index of a dewaxed product of waxy hydrocarbon feeds comprising contacting the catalyst with a waxy hydrocarbon feed under isomerization dewaxing conditions.

13. The process of claim 12 wherein the molecular sieve is predominantly in the hydrogen form.

14. The process of claim 1 wherein the process is a process for producing a C$_{20+}$ lube oil from a C$_{20+}$ olefin feed comprising isomerizing said olefin feed under isomerization conditions over the catalyst.

15. The process of claim 14 wherein the molecular sieve is predominantly in the hydrogen form.

16. The process of claim 14 wherein the catalyst further comprises at least one Group VIII metal.

17. The process of claim 1 wherein the process is a process for catalytically dewaxing a hydrocarbon oil feedstock boiling above about 350° F. (177° C.) and containing straight chain and slightly branched chain hydrocarbons comprising contacting said hydrocarbon oil feedstock in the presence of added hydrogen gas at a hydrogen pressure of about 15-3000 psi (0.103-20.7 MPa) under dewaxing conditions with the catalyst.

18. The process of claim 17 wherein the molecular sieve is predominantly in the hydrogen form.

19. The process of claim 17 wherein the catalyst further comprises at least one Group VIII metal.

20. The process of claim 17 wherein said catalyst comprises a layered catalyst comprising a first layer comprising the molecular sieve and at least one Group VIII metal, and a second layer comprising an aluminosilicate molecular sieve which is more shape selective than the molecular sieve of said first layer.

21. The process of claim 1 wherein the process is a process for preparing a lubricating oil which comprises:
hydrocracking in a hydrocracking zone a hydrocarbonaceous feedstock to obtain an effluent comprising a hydrocracked oil; and
catalytically dewaxing said effluent comprising hydrocracked oil at a temperature of at least about 400° F. (204° C.) and at a pressure of from about 15 psig to about 3000 psig (0.103 to 20.7 MPa gauge) in the presence of added hydrogen gas with the catalyst.

22. The process of claim 21 wherein the molecular sieve is predominantly in the hydrogen form.

23. The process of claim 21 wherein the catalyst further comprises at least one Group VIII metal.

24. The process of claim 1 wherein the process is a process for isomerization dewaxing a raffinate comprising contacting said raffinate in the presence of added hydrogen under isomerization dewaxing conditions with the catalyst.

25. The process of claim 24 wherein the molecular sieve is predominantly in the hydrogen form.

26. The process of claim 24 wherein the catalyst further comprises at least one Group VIII metal.

27. The process of claim 24 wherein the raffinate is bright stock.

28. The process of claim 1 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

29. The process of claim 28 wherein the molecular sieve is substantially free of acid.

30. The process of claim 28 wherein the molecular sieve contains a Group VIII metal component.

31. The process of claim 1 wherein the process is a catalytic cracking process comprising contacting a hydrocarbon feedstock in a reaction zone under catalytic cracking conditions in the absence of added hydrogen with the catalyst.

32. The process of claim 31 wherein the molecular sieve is predominantly in the hydrogen form.

33. The process of claim 31 wherein the catalyst additionally comprises a large pore crystalline cracking component.

34. The process of claim 1 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

35. The process of claim 34 wherein the molecular sieve is predominantly in the hydrogen form.

36. The process of claim 34 wherein the molecular sieve has been impregnated with at least one Group VIII metal.

37. The process of claim 34 wherein the catalyst has been calcined in a steam/air mixture at an elevated temperature after impregnation of the Group VIII metal.

38. The process of claim 36 wherein the Group VIII metal is platinum.

39. The process of claim 1 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

40. The process of claim 39 wherein the molecular sieve is predominantly in the hydrogen form.

41. The process of claim 39 wherein the olefin is a $C_2$ to $C_4$ olefin.

42. The process of claim 41 wherein the aromatic hydrocarbon and olefin are present in a molar ratio of about 4:1 to about 20:1, respectively.

43. The process of claim 41 wherein the aromatic hydrocarbon is selected from the group consisting of benzene, toluene, ethylbenzene, xylene, naphthalene, naphthalene derivatives, dimethylnaphthalene or mixtures thereof.

44. The process of claim 1 wherein the process is a process for alkylating an aromatic hydrocarbon which comprises contacting under alkylation conditions an aromatic hydrocarbon with a $C_{20+}$ olefin under at least partial liquid phase conditions and in the presence of the catalyst.

45. The process of claim 44 wherein the molecular sieve is predominantly in the hydrogen form.

46. The process of claim 45 wherein the aromatic hydrocarbon and olefin are present in a molar ratio of about 1:15 to about 25:1, respectively.

47. The process of claim 45 wherein the aromatic hydrocarbon is selected from the group consisting of benzene, toluene, ethylbenzene, xylene, naphthalene, naphthalene derivatives, dimethylnaphthalene or mixtures thereof.

48. The process of claim 1 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

49. The process of claim 48 wherein the molecular sieve is predominantly in the hydrogen form.

50. The process of claim 48 wherein the aromatic hydrocarbon and the polyalkyl aromatic hydrocarbon are present in a molar ratio of from about 1:1 to about 25:1, respectively.

51. The process of claim 48 wherein the aromatic hydrocarbon is selected from the group consisting of benzene, toluene, ethylbenzene, xylene, or mixtures thereof.

52. The process of claim 44 wherein the polyalkyl aromatic hydrocarbon is a dialkylbenzene.

53. The process of claim 1 wherein the process is a process to convert paraffins to 5 aromatics which comprises contacting paraffins under conditions which cause paraffins to convert to aromatics with a catalyst comprising the molecular sieve and gallium, zinc, or a compound of gallium or zinc.

54. The process of claim 1 wherein the process is a process for isomerizing olefins comprising contacting said olefin under conditions which cause isomerization of the olefin with the catalyst.

55. The process of claim 1 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

56. The process of claim 1 wherein the process is a process for oligomerizing olefins comprising contacting an olefin feed under oligomerization conditions with the catalyst.

57. The process of claim 1 wherein the process is a process for the production of higher molecular weight hydrocarbons from lower molecular weight hydrocarbons comprising the steps of:
  (a) introducing into a reaction zone a lower molecular weight hydrocarbon-containing gas and contacting said gas in said zone under $C_{2+}$ hydrocarbon synthesis conditions with the catalyst and a metal or metal compound capable of converting the lower molecular weight hydrocarbon to a higher molecular weight hydrocarbon; and
  (b) withdrawing from said reaction zone a higher molecular weight hydrocarbon-containing stream.

58. The process of claim 57 wherein the metal or metal compound comprises a lanthanide or actinide metal or metal compound.

59. The process of claim 57 wherein the lower molecular weight hydrocarbon is methane.

60. A process for converting oxygenated hydrocarbons comprising contacting said oxygenated hydrocarbon under conditions to produce liquid products with a catalyst comprising a molecular sieve having a mole ratio greater than about 15 of (1) an oxide of a first tetravalent element to (2) an oxide of a trivalent element, pentavalent element, second tetravalent element different from said first tetravalent element or mixture thereof having, after calcination, the X-ray diffraction lines of Table II.

61. The process of claim 1 wherein the molecular sieve has a mole ratio greater than about 15 of (1) an oxide of silicon, germanium or mixtures thereof to (2) an oxide of aluminum, gallium, iron, boron, titanium, indium, vanadium or mixtures thereof.

62. The process of claim 61 wherein the molecule sieve has a micropore volume of at least 0.10.

63. The process of claim 61 wherein the molecular sieve has a Constraint Index of less than or equal to 2.0.

64. The process of claim 61 wherein the oxygenated hydrocarbon is a lower alcohol.

65. The process of claim 64 wherein the lower alcohol is methanol.

* * * * *